(12) United States Patent
Tsubota et al.

(10) Patent No.: US 8,770,743 B2
(45) Date of Patent: Jul. 8, 2014

(54) EYEWEAR

(75) Inventors: Kazuo Tsubota, Chiba (JP); Hitoshi Tanaka, Gunma (JP)

(73) Assignee: Jin Co., Ltd., Gunma (JP)

( * ) Notice: Subject to any disclaimer, the term of this patent is extended or adjusted under 35 U.S.C. 154(b) by 85 days.

(21) Appl. No.: 13/299,357

(22) Filed: Nov. 18, 2011

(65) Prior Publication Data

US 2012/0162598 A1 Jun. 28, 2012

(30) Foreign Application Priority Data

Dec. 27, 2010 (JP) ................................. 2010-291309

(51) Int. Cl.
*G02C 11/00* (2006.01)
*G02C 5/00* (2006.01)

(52) U.S. Cl.
CPC ...................................... *G02C 5/001* (2013.01)
USPC ........................................................ 351/158

(58) Field of Classification Search
CPC ........ G02C 5/001; G02C 5/008; G02C 11/08; G02C 11/10
USPC ................................................... 351/41, 158
See application file for complete search history.

(56) References Cited

U.S. PATENT DOCUMENTS 5,368,582 A * 11/1994 Bertera .......................... 604/295
5,539,480 A * 7/1996 Rakoff et al. .................. 351/158
5,627,611 A * 5/1997 Scheiner ....................... 351/158
6,641,264 B1 * 11/2003 Schwebel ....................... 351/62
6,908,195 B2 * 6/2005 Fuller ............................. 351/158
2005/0001981 A1 * 1/2005 Anderson et al. ............. 351/209
2009/0247967 A1 * 10/2009 Delli Paoli, Jr. .............. 604/300

FOREIGN PATENT DOCUMENTS

| CN | 200991498 Y | 12/2007 |
|---|---|---|
| JP | 2543974 Y2 | 5/1997 |
| JP | 3050959 U | 5/1998 |
| JP | 2000-005215 A | 1/2000 |
| JP | 1069214 S | 5/2000 |
| JP | 3152412 U | 7/2009 |

OTHER PUBLICATIONS

International Preliminary Report on Patentability for International application No. PCT/JP2011/004532, issued by the International Bureau of WIPO on Jul. 11, 2013.
International Search Report for International Application No. PCT/JP2011/004532, issued by the Japanese Patent Office on Sep. 6, 2011.
Notification of the First Office Action for Chinese Patent Application No. 201180062924.9, issued by the State Intellectual Property office of the PRC on Jan. 20, 2014.

* cited by examiner

*Primary Examiner* — Darryl J Collins (57) ABSTRACT

Eyewear comprising a frame and a liquid storage portion that is disposed within the frame and that includes a cavity for storing liquid. The liquid storage portion includes a gas passing section that allows gas to pass therethrough from the cavity to an inside surface of the frame, which is a surface facing a head of a wearer when the frame is worn on the head, but does not allow liquid to pass therethrough from the cavity to the inside surface of the frame. The liquid storage portion may be disposed such that an outer surface of the liquid storage portion is further inside the frame than an outer surface of the frame.

23 Claims, 13 Drawing Sheets

EYEWEAR

The contents of the following Japanese patent application are incorporated herein by reference: No. 2010-291309 filed on Dec. 27, 2010.

BACKGROUND

1. Technical Field

The present invention relates to eyewear.

2. Related Art

There are glasses known for preventing allergies and dry eye, and these glasses have a frame that includes a humidifier having a container that houses a liquid holding component. For example, see Patent Documents 1 to 3.

Patent Document 1: Japanese Patent Application Publication No. 2000-005215
Patent Document 2: Japanese Examined Utility Model Registration No. 3152412
Patent Document 3: Japanese Design Registration No. 1069214

However, since the entire space of the container is filled with the liquid holding component, the amount of liquid that can be stored in the container is decreased. Therefore, it is an object of an aspect of the innovations herein to provide eyewear that is capable of overcoming the above drawbacks accompanying the related art. The above and other objects can be achieved by combinations described in the independent claims. The dependent claims define further advantageous and exemplary combinations of the innovations herein.

SUMMARY

In order to solve the above problem, according to a first aspect related to the innovations herein, provided is eyewear comprising a frame and a liquid storage portion that is disposed within the frame and that includes a cavity for storing liquid. The liquid storage portion includes a gas passing section that allows gas to pass therethrough from the cavity to an inside surface of the frame, which is a surface facing a head of a wearer when the frame is worn on the head, but does not allow liquid to pass therethrough from the cavity to the inside surface of the frame.

The liquid storage portion may be disposed such that an outer surface of the liquid storage portion is further inside the frame than an outer surface of the frame. The liquid storage portion may include a gas permeable hole that is formed in an inside surface thereof, which is a surface facing the head of the wearer when the frame is worn on the head, that penetrates from the cavity to the inside surface of the liquid storage portion, and that allows gas to pass therethrough but does not allow liquid to pass therethrough.

The liquid storage portion may be disposed in a temple, an ear band, or an end piece of the frame. A plurality of the gas permeable holes may be formed in the inside surface of the liquid storage portion. When the frame is worn on the head, distance from a bottommost portion of the gas permeable holes to a bottommost portion of whichever of the temple, the ear band, or the end piece of the frame the liquid storage portion is disposed in may be greater than distance from a topmost portion of the gas permeable holes to a topmost portion of whichever of the temple, the ear band, or the end piece of the frame the liquid storage portion is disposed in. The liquid storage portion may be detachable from the frame.

The summary clause does not necessarily describe all necessary features of the embodiments of the present invention. The present invention may also be a sub-combination of the features described above.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention. The following describes embodiments of the present invention using drawings, and portions that are identical or similar are given the same reference numerals. The drawings are schematic views, and do not indicate the actual dimensions of the embodiments. For ease of explanation, different drawings may include portions in different scales.

Figure 1:
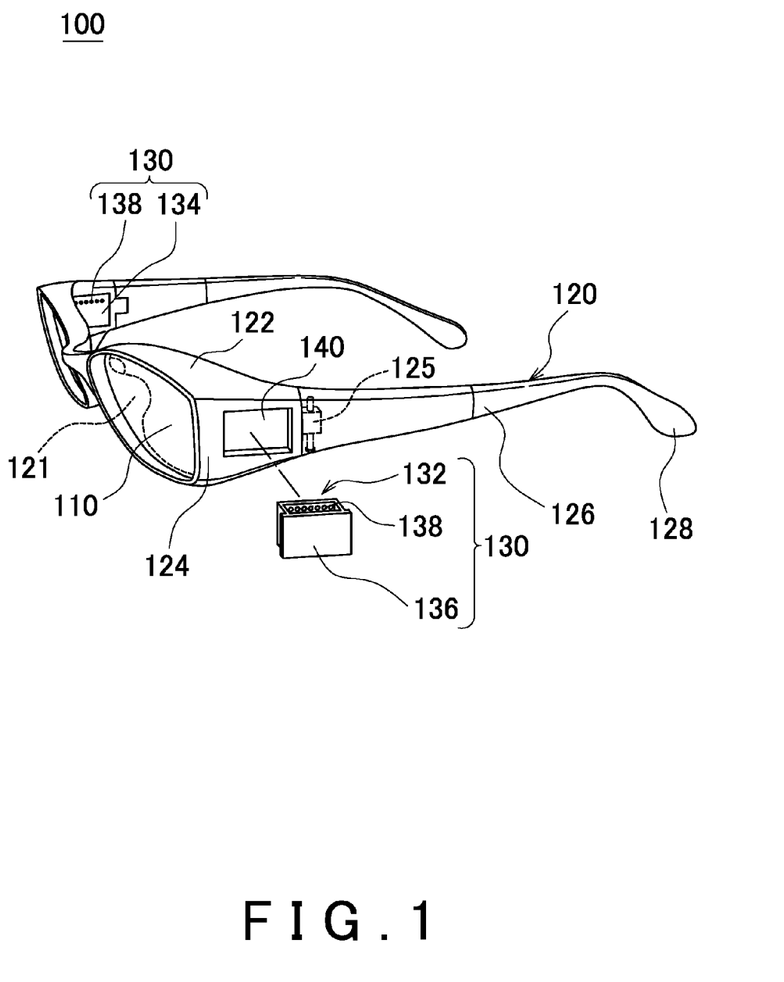
FIG. 1 is a schematic view of exemplary glasses 100.

FIG. 1 is a schematic view of exemplary glasses 100. The glasses 100 include a pair of lenses 110, a frame 120, and liquid containers 130. The glasses 100 and the frame 120 may be an example of eyewear. Each liquid container 130 may be an example of a liquid storage portion. In the present embodiment, openings 140 are formed in portions of the frame 120, and the liquid containers 130 can be inserted into and removed from the openings 140. For ease of explanation, the following description deals with only the left-eye side of the glasses 100, but the right-eye side of the glasses 100 has the same configuration.

The frame 120 may include a nose pad 121, a rim 122, an end piece 124, a hinge 125, a temple 126, and an ear band 128. The nose pad 121 positions the frame 120 relative to the face of a wearer. The rim 122 supports the lens 110. The rim 122 may include a hood portion that extends from the periphery of the lens 110 toward the wearer. Therefore, the dispersion of evaporated gas from the liquid container 130 can be contained. The end piece 124 is arranged at the edge of the rim 122 and connects to the temple 126 via the hinge 125. The temple 126 sandwiches the head of the wearer together with the temple 126 on the right-eye side. The ear band 128 covers at least a portion of the temple 126.

The liquid container 130 contains a liquid. A cavity 132 that can hold the liquid is formed within the liquid container 130. The inner surface of the cavity 132 may be processed to be water repellent. The inner surface of the cavity 132 may also undergo antibacterial processing.

The liquid container 130 may be inserted into and removed from the frame 120. The liquid container 130 may be disposed in at least one of the nose pad 121, the rim 122, the end piece 124, the temple 126, and the ear band 128 of the frame 120.

At least a portion of the liquid container 130 may be disposed within the frame 120. The liquid container 130 may be disposed such that the outer surface of the liquid container 130 is further within the frame 120 than the outer surface of the frame 120. For example, with "top surface" referring to a surface that is on top when the frame 120 is worn on the head, the top surface of the liquid container 130 may be arranged below the top surface of the frame 120, and the bottom surface of the liquid container 130 may be arranged above the bottom surface of the frame 120. In this way, damage to the liquid container 130 can be prevented.

In the present embodiment, the liquid container 130 includes a side surface 134 that is arranged on the side facing the head of the wearer, when the frame 120 into which the liquid container 130 is inserted is worn (referred to hereinafter as the "inside" of the frame 120), and a side surface 136 that is arranged opposite the side surface 134. The side surface 134 and the side surface 136 may have shapes corresponding to the side surfaces of the frame 120. The side surface 134 and the side surface 136 may be arranged further within the frame 120 than the side surface of the frame 120.

The side surface 134 of the liquid container 130 includes a gas permeable hole 138 that penetrates from the cavity 132 to the side surface 134, and that allows gas to pass therethrough but does not allow liquid to pass therethrough. The gas permeable hole 138 allows the gas generated by the evaporation of the liquid stored in the cavity 132 to pass from the cavity 132 to the inside surface of the frame 120. The gas permeable hole 138 does not allow liquid to pass from the cavity 132 to the inside surface of the frame 120. The gas permeable hole 138 may be an example of a gas passing section that allows gas to pass from the cavity 132 to the inside surface of the frame 120, but does not allow liquid to pass from the cavity 132 to the inside surface of the frame 120.

In this way, the leakage of liquid from the gas permeable hole 138 can be restricted. For example, the gas permeable hole 138 can prevent leakage of the liquid even if the gas permeable hole 138 is not covered with a water retentive or water absorbent material such as felt, paper, a sea sponge, a sponge, a hydrophilic polymer, or a hydrogel. Furthermore, the liquid container 130 can hold a greater amount of liquid than when the entire liquid container is filled with a water retentive or water absorbent material. Yet further, since the leakage of liquid from the gas permeable hole 138 can be restricted even when the liquid container 130 is not filled with a large amount of water retentive or water absorbent material, the glasses 100 can be used hygienically.

The shape of the gas permeable hole 138 may be determined such that water vapor can pass from the cavity 132 to the inside surface of the frame 120 but pure water and tap water cannot pass from the cavity 132 to the inside surface of the frame 120. Exemplary characteristics for determining the shape of the gas permeable hole 138 may include the cross-sectional shape of the gas permeable hole 138, the cross-sectional size of the gas permeable hole 138, and the length of the gas permeable hole 138 from the surface of the cavity 132 to the inside surface of the frame 120. Whether or not the gas permeable hole 138 allows water vapor to pass therethrough can be determined by measuring the amount of water vapor passing through a test piece, using the water vapor permeability test (cup method) defined in JIS Z0208 or the water vapor permeability test (Lyssy method, etc.) defined in JIS K7129. If the amount of water vapor passed when the gas permeable hole 138 is provided in the test piece is greater than the amount of water vapor passed when the gas permeable hole 138 is not provided in the test piece, the gas permeable hole 138 may be judged as allowing water vapor to pass therethrough.

Whether or not the gas permeable hole 138 allows pure water or tap water to pass therethrough can be determined based on whether pure water or tap water passes through the gas permeable hole 138 during a 10 minute period during which a pressure difference of no more than 9.806 Pa is created between the opening of the gas permeable hole 138 on the cavity 132 side and the opening of the gas permeable hole 138 on the inside surface of the frame 120. Whether or not the gas permeable hole 138 allows pure water or tap water to pass therethrough may be determined based on observing whether there is water leakage. The pressure difference used in the above determination is preferably greater than 9.806 Pa and no greater than 49.03 Pa, more preferably greater than 49.03 Pa and no greater than 98.06 Pa, and most preferably greater than 98.06 Pa and no greater than 294.18 Pa.

If the gas permeable hole 138 has a circular cross section, the diameter of the gas permeable hole 138 is no less than 0.1 mm and no greater than 1.5 mm, preferably no less than 0.3 mm and no greater than 1.2 mm, and more preferably no less than 0.5 mm and no greater than 1 mm. If the gas permeable hole 138 has an elliptical cross section, the long diameter of the gas permeable hole 138 is no less than 0.1 mm and no greater than 1.7 mm, preferably no less than 0.5 mm and no greater than 1.4 mm, and more preferably no less than 0.7 mm and no greater than 1.2 mm. The length of the gas permeable hole 138 from the surface on the cavity 132 side to the surface on the inside of the frame 120 is no less than 0.1 mm and no greater than 1.5 mm, preferably no less than 0.3 mm and no greater than 1.2 mm, and more preferably no less than 0.5 mm and no greater than 1 mm.

The side surface 134 of the liquid container 130 may include a plurality of the gas permeable holes 138. The total surface area of the openings of the gas permeable holes 138 provided in the side surface 134 on the inside of the frame 120 is, for example, no less than 0.018 $cm^2$, preferably no less than 0.027 $cm^2$, and more preferably no less than 0.044 $cm^2$. In this way, the liquid stored in the cavity 132 can be sufficiently evaporated. If the total surface area of the openings of the gas permeable holes 138 is less than 0.018 $cm^2$, it is difficult to quickly humidify the air around the eyes of the wearer.

The total volume of the gas permeable holes 138 may be less than the volume of the cavity 132. If a filler is disposed within the cavity 132, the volume of the portion occupied by the filler within the cavity 132 is not included in the volume of the cavity 132. The filler may be a water retentive or water absorbent material such as felt, paper, a sea sponge, a sponge, a hydrophilic polymer, or a hydrogel, for example.

When the frame 120 is worn on the head of the wearer, the distance between the bottommost portion of the gas permeable holes 138 and the bottommost portion of the components of the frame 120 in which the liquid container 130 is disposed may be greater than the distance between the uppermost portion of the gas permeable holes 138 and the uppermost portion of the frame 120 in which the liquid container 130 is disposed. As a result, even when the size of the gas permeable holes 138 is increased, the leakage of the liquid can be restricted when the liquid container 130 is inclined.

The gas permeable hole 138 may be disposed at a position that is above the position of the liquid surface when the frame 120 in which the liquid container 130 is disposed is worn on the head. If the gas permeable hole 138 is sufficiently small, the gas permeable hole 138 may be arranged at a position below the position of the liquid surface when the frame 120 in which the liquid container 130 is disposed is worn on the head.

With the configuration described above, the gas generated by the evaporation of the liquid stored in the cavity 132 is supplied to the inside of the frame 120 through the gas permeable hole 138. Furthermore, since the gas permeable hole 138 does not pass the liquid stored in the cavity 132, the liquid is prevented from splashing onto the face of the user.

In the present embodiment, the glasses 100 are used as an example of the eyewear, but the eyewear is not limited to this example. The eyewear may be any accessory related to the eyes, and may be a facial accessory or head accessory such as glasses, sun glasses, goggles, or a head-mounted display. The eyewear may be the frame of a facial accessory or head accessory, or may be a portion of this frame.

In the present embodiment, the liquid storage portion is the liquid container 130 that can be inserted into and removed from the opening 140 in the frame 120, but the liquid storage portion is not limited to this example. The liquid storage portion may be disposed in a recessed portion formed in the frame 120. The liquid storage portion may be a portion of the frame in which a cavity is formed. The liquid storage portion may be the nose pad, the rim, the end piece, the temple, or the ear band in which a cavity is formed.

In the present embodiment, the gas permeable hole 138 is used as an example of the gas passing section, but the gas passing section is not limited to this example. The gas passing section may include an organic polymer film or an inorganic porous film that allows gas to pass therethrough but does not allow liquid to pass therethrough. The gas passing section may include an organic polymer film or an inorganic porous film that allows water vapor to pass therethrough but does not allow pure water or tap water to pass therethrough. The gas passing section may be silicone rubber.

As a result, the leakage of liquid from the gas permeable hole 138 can be restricted. For example, the leakage of liquid from the gas permeable hole 138 can be restricted even when the gas permeable hole 138 is not covered with a water retentive or water absorbent material. In this case, a greater amount of liquid can be stored, and the glasses 100 can be used hygienically.

In the present embodiment, a water retentive or water absorbent material is not disposed within the cavity 132, but the glasses 100 are not limited to this configuration. A water retentive or water absorbent material such as felt, paper, a sea sponge, a sponge, a hydrophilic polymer, or a hydrogel may be used as a portion of the gas passing section. A water retentive or water absorbent material may be disposed within the cavity 132. As a result, leakage of liquid from the cavity 132 can be restricted even when the gas permeable hole 138 is large. In this case, the top end of the water retentive or water absorbent material is preferably arranged above the liquid surface of the liquid stored in the cavity.

If the water retentive or water absorbent material is disposed within the cavity 132, the volume occupied by the water retentive or water absorbent material within the cavity 132 may be less than half the volume of the cavity 132. As a result, the cavity 132 can store a greater amount of liquid.

Figure 2:
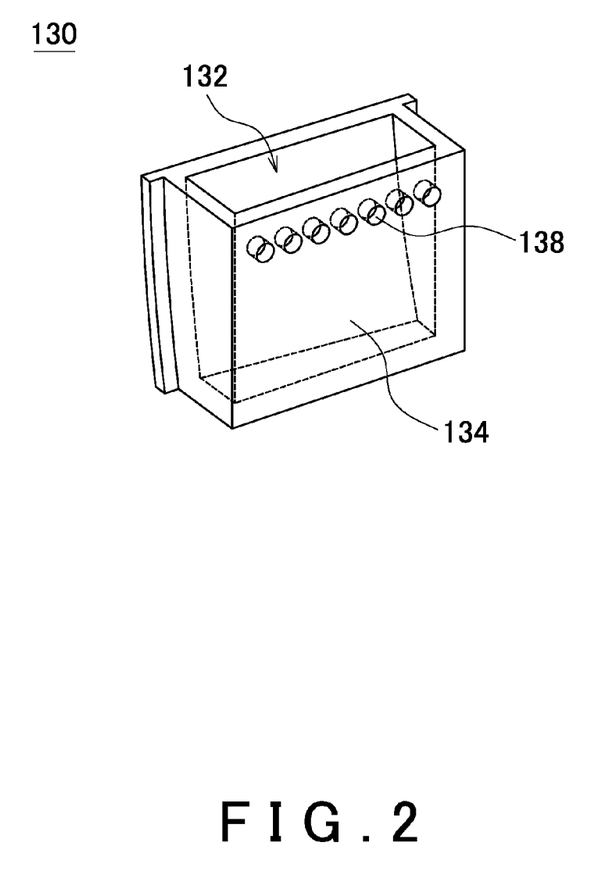
FIG. 2 schematically shows an exemplary perspective view of the liquid container 130.
Figure 3:
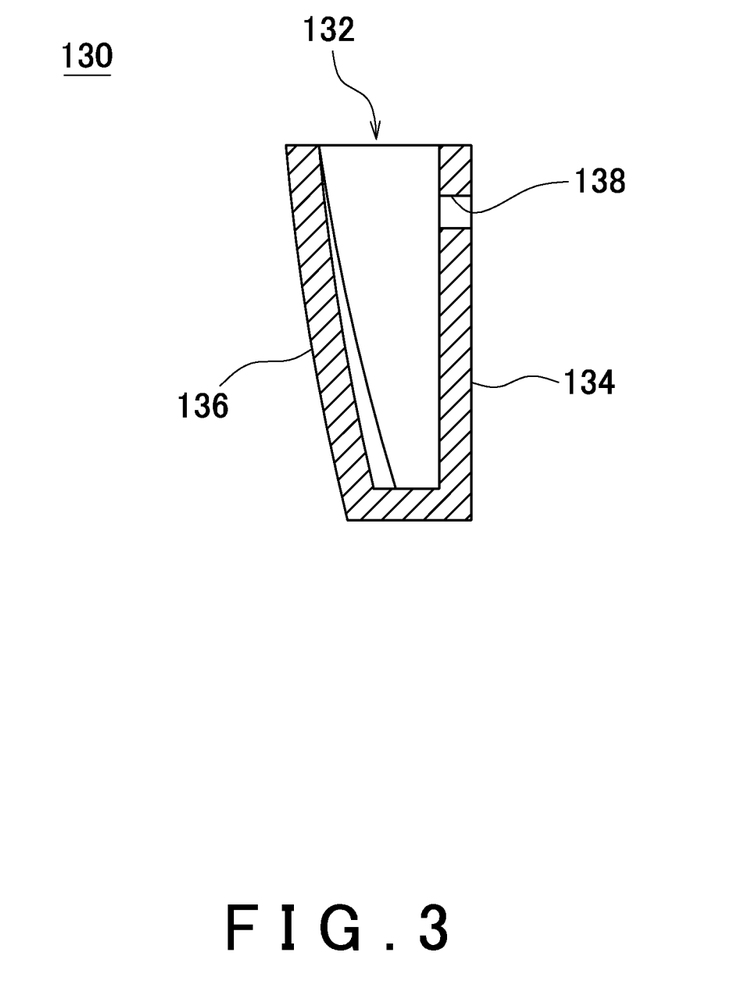
FIG. 3 schematically shows an exemplary cross section of the liquid container 130.

FIG. 2 schematically shows an exemplary perspective view of the liquid container 130. FIG. 3 schematically shows an exemplary cross section of the liquid container 130. In FIGS. 2 and 3, the cross section resulting from the liquid container 130 being cut by a plane perpendicular to the side surface 134 is seen from the left side. The top surface of the frame 120 in which the liquid container 130 is disposed when worn on the head is shown at the top in FIGS. 2 and 3. The following describes the liquid container 130 using FIGS. 2 and 3.

In the present embodiment, the liquid container 130 is disposed in the opening 140 formed in the end piece 124 of the frame 120. The side surface 134 of the liquid container 130 includes a plurality of gas permeable holes 138. The gas permeable holes 138 penetrate through the side surface 134 to connect the cavity 132 to the outside of the liquid container 130. The distance between the bottommost portions of the gas permeable holes 138 and the bottommost portion of the end piece 124 may be greater than the distance between the topmost portions of the gas permeable holes 138 and the topmost portion of the end piece 124. An opening is formed in the top portion of the liquid container 130, thereby exposing the cavity 132 to the outside. The shape of the side surface 136 may conform to the shape of the end piece 124. The side surface 136 need not be parallel to the side surface 134.

In the present embodiment, the opening is formed in the top portion of the liquid container 130 and the cavity 132 is exposed to the outside, but the liquid container 130 is not limited to this configuration. A lid may be disposed to block the opening formed in the top portion of the liquid container 130. The material used for the lid may be an elastomer such as natural rubber, synthesized rubber, or silicone rubber. In this case, since the lid is elastic, the lid can be arranged between the liquid container 130 and the opening 140 of the frame 120 to press against both the liquid container 130 and the frame 120, thereby restricting leakage from the liquid container 130 through the opening 140.

Figure 4:
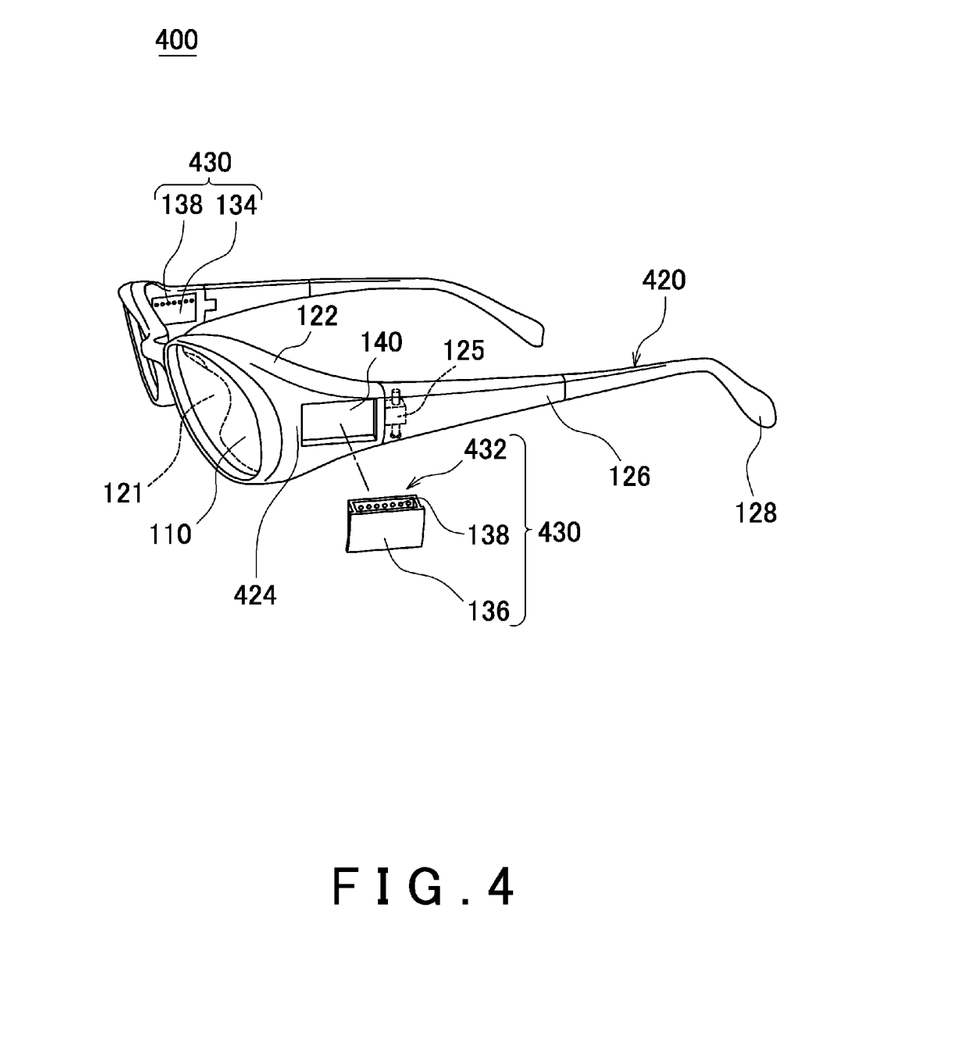
FIG. 4 is a schematic view of glasses 400.
Figure 5:
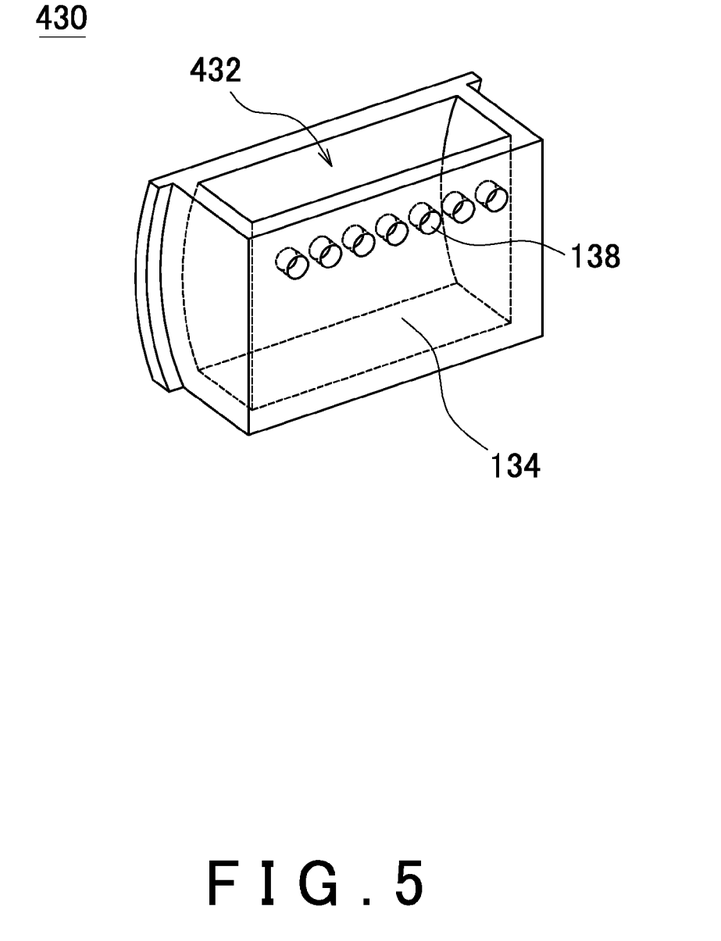
FIG. 5 schematically shows an exemplary perspective view of a liquid container 430.
Figure 6:
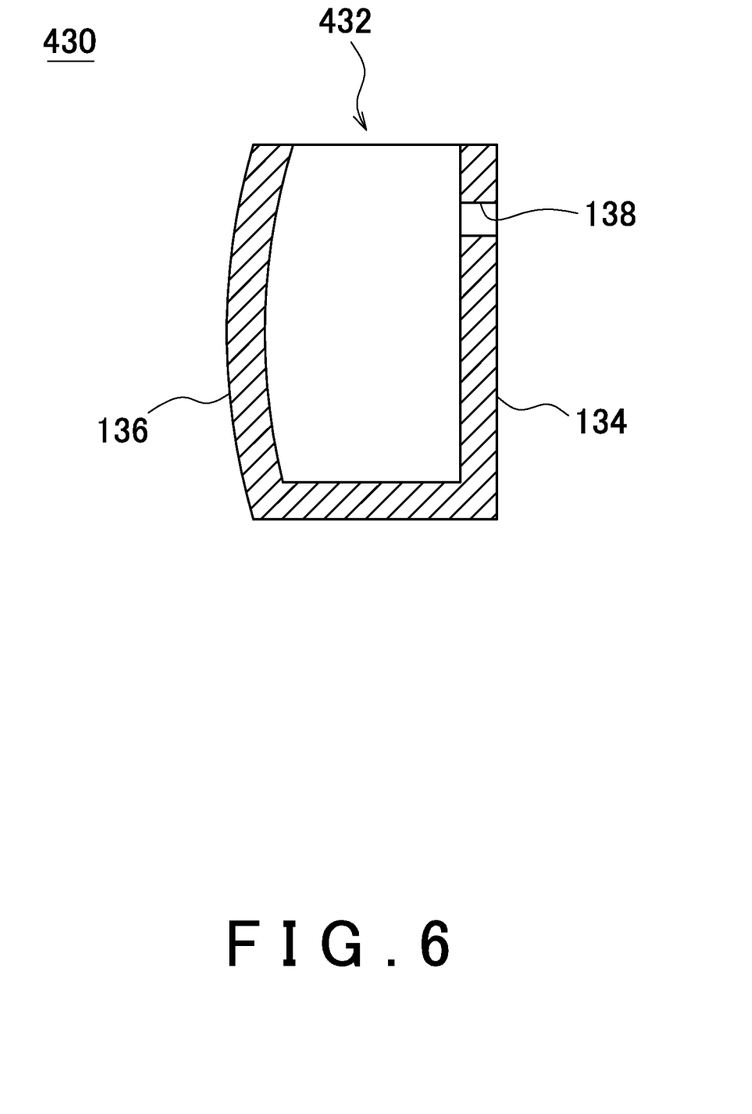
FIG. 6 schematically shows an exemplary cross section of the liquid container 430.

FIG. 4 is a schematic view of glasses 400. FIG. 5 schematically shows an exemplary perspective view of a liquid container 430. FIG. 6 schematically shows an exemplary cross section of the liquid container 430. FIG. 6 shows the cross section of the liquid container 430 as seen from the left side when the liquid container 430 is cut by a plane that is parallel to the vertical direction of FIG. 5 and perpendicular to the side surface 134. The top of a frame 420 in which the liquid container 430 is disposed when worn on the head is shown at the top in FIGS. 4, 5, and 6.

The following describes the glasses 400 using FIGS. 4, 5, and 6. The glasses 400 include the pair of lenses 110, the frame 420, and the liquid containers 430. The glasses 400 and the frame 420 may be an example of eyewear. Each liquid container 430 may be an example of a liquid storage portion. Components that are the same as those of the glasses 100 are given the same reference numerals, and further description is omitted. For ease of explanation, the following description deals with only the left-eye side of the glasses 400, but the right-eye side of the glasses may have the same configuration.

The frame 420 may include the nose pad 121, the rim 122, an end piece 424, the hinge 125, the temple 126, and the ear band 128. The frame 420 may have the same configuration as the frame 120, and a redundant description of this configuration is omitted. A cavity 432 that can store liquid is formed within the liquid container 430. The liquid container 430 can be inserted into and removed from the frame 420. The liquid container 430 may have the same configuration as the liquid container 130, and a redundant description of this configuration is omitted.

The glasses 400 differ from the glasses 100 in that the end piece 424 and the liquid container 430 have different shapes. The side surface 136 of the liquid container 430 protrudes toward the outside of the cavity 432 and the shape of the end piece 424 conforms to the shape of the side surface 136. As a result, the liquid container 430 can store a greater amount of liquid than the liquid container 130.

Figure 7:
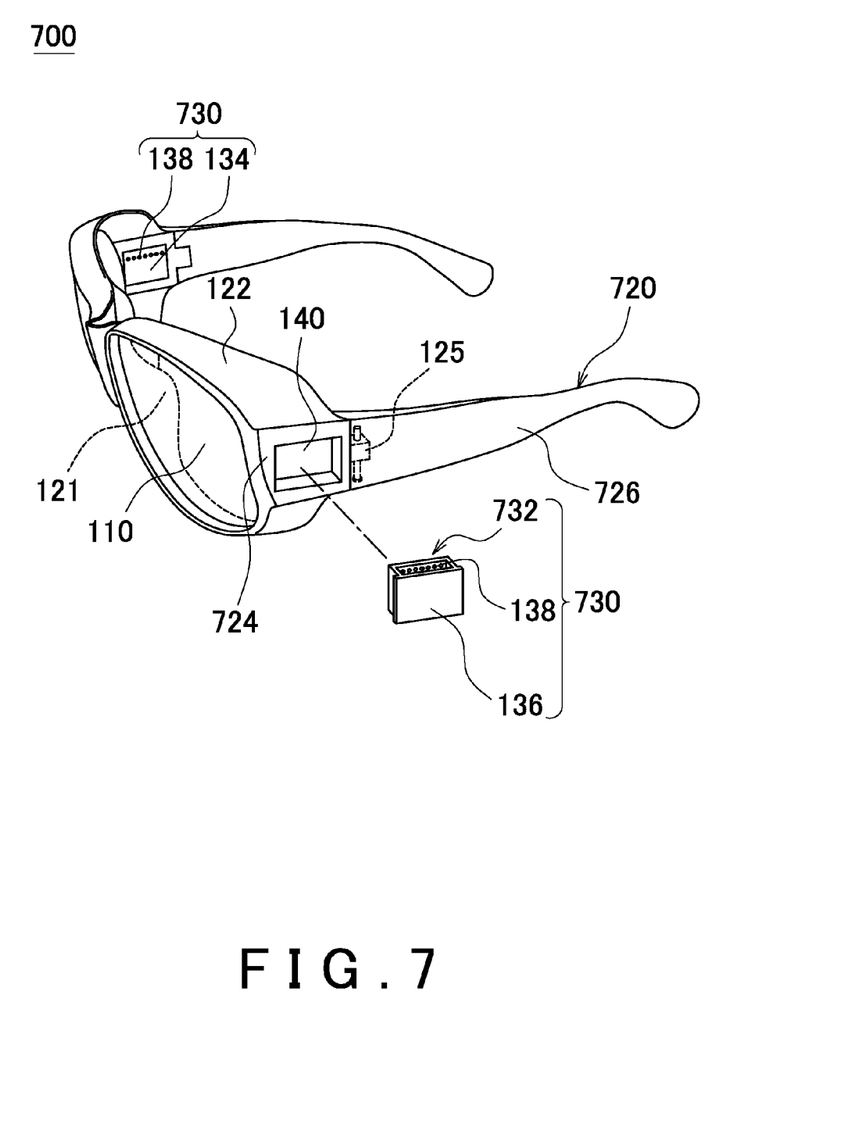
FIG. 7 is a schematic view of exemplary glasses 700.
Figure 8:
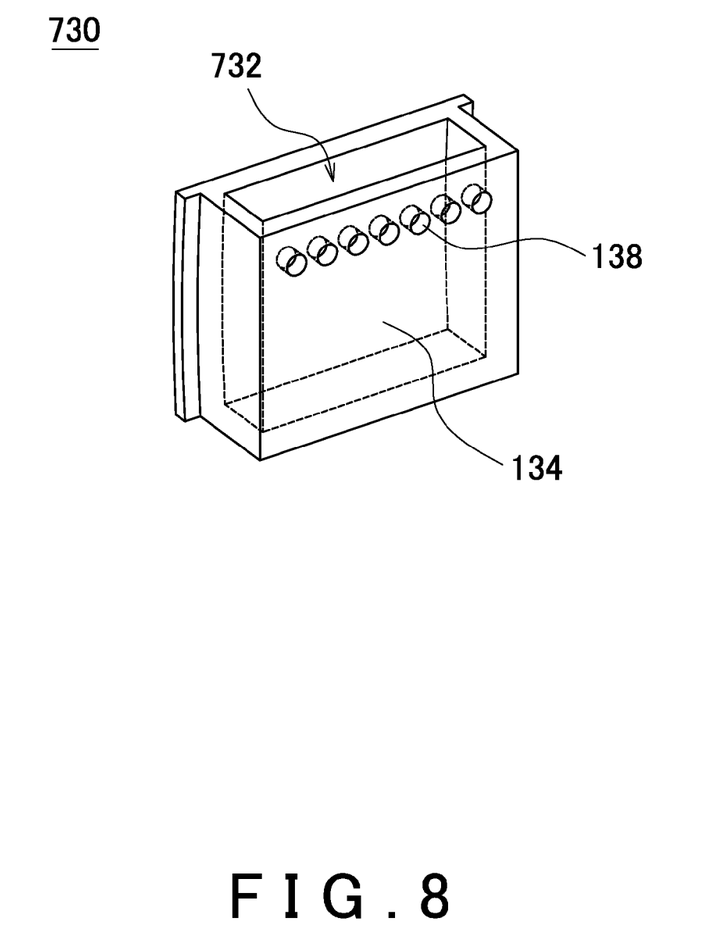
FIG. 8 schematically shows an exemplary perspective view of a liquid container 730.
Figure 9:
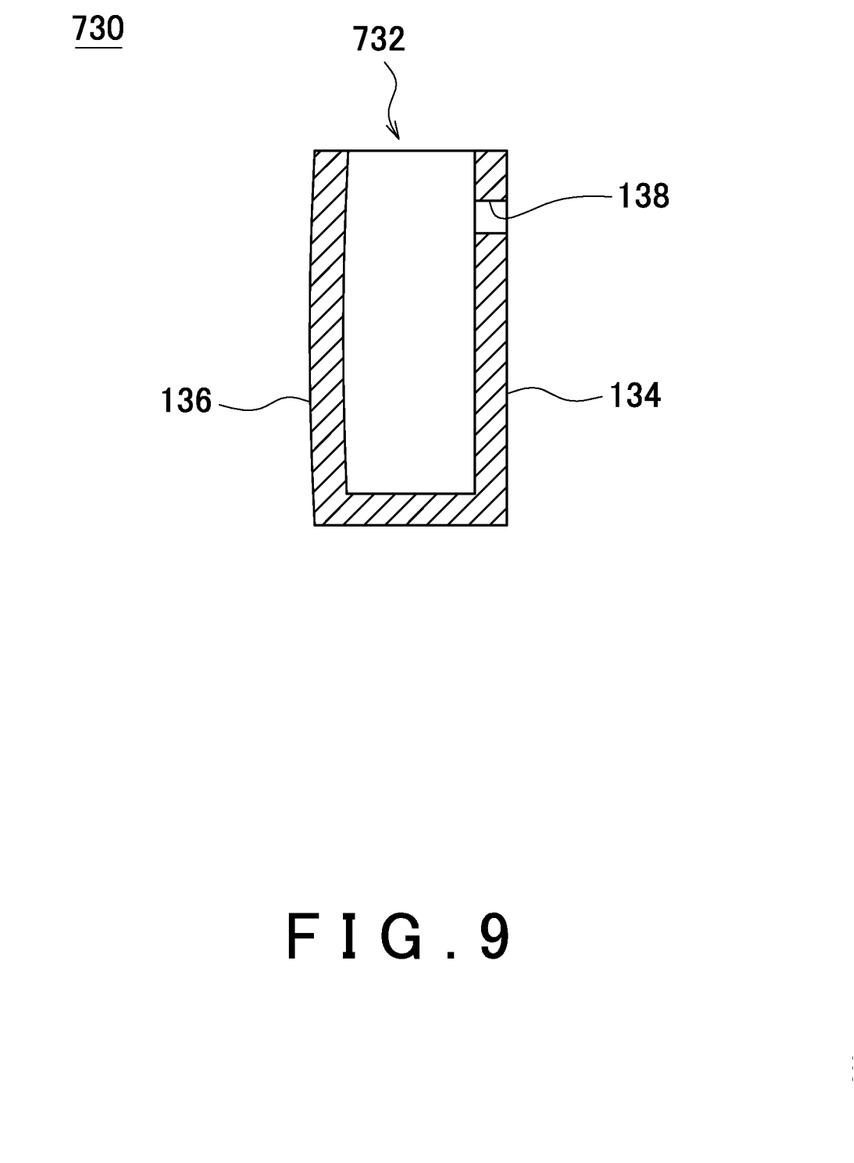
FIG. 9 schematically shows an exemplary cross section of the liquid container 730.

FIG. 7 is a schematic view of exemplary glasses 700. FIG. 8 schematically shows an exemplary perspective view of a liquid container 730. FIG. 9 schematically shows an exemplary cross section of the liquid container 730. FIG. 9 shows the cross section of the liquid container 730 as seen from the left side when the liquid container 730 is cut by a plane that is parallel to the vertical direction of FIG. 8 and perpendicular to the side surface 134. The top of a frame 720 in which the liquid container 730 is disposed when worn on the head is shown at the top in FIGS. 7, 8, and 9.

The following describes the glasses 700 using FIGS. 7, 8, and 9. The glasses 700 include the pair of lenses 110, the frame 720, and the liquid containers 730. The glasses 700 and the frame 720 may be an example of eyewear. Each liquid container 730 may be an example of a liquid storage portion. Components that are the same as those of the glasses 100 are given the same reference numerals, and further description is omitted. For ease of explanation, the following description deals with only the left-eye side of the glasses 700, but the right-eye side of the glasses may have the same configuration.

The frame 720 may include the nose pad 121, the rim 122, an end piece 724, the hinge 125, and a temple 726. The frame 720 may have the same configuration as the frame 120, and a redundant description of this configuration is omitted. A cavity 732 that can store liquid is formed within the liquid container 730. The liquid container 730 can be inserted into and removed from the frame 720. The liquid container 730 may have the same configuration as the liquid container 130, and a redundant description of this configuration is omitted.

The glasses 700 differ from the glasses 100 in that the end piece 724 and the liquid container 730 have different shapes. The side surface 136 of the liquid container 730 is substantially parallel to the side surface 134 and the shape of the end piece 724 conforms to the shape of the side surface 136. As a result, the liquid container 730 can store a greater amount of liquid than the liquid container 130.

Figure 10:
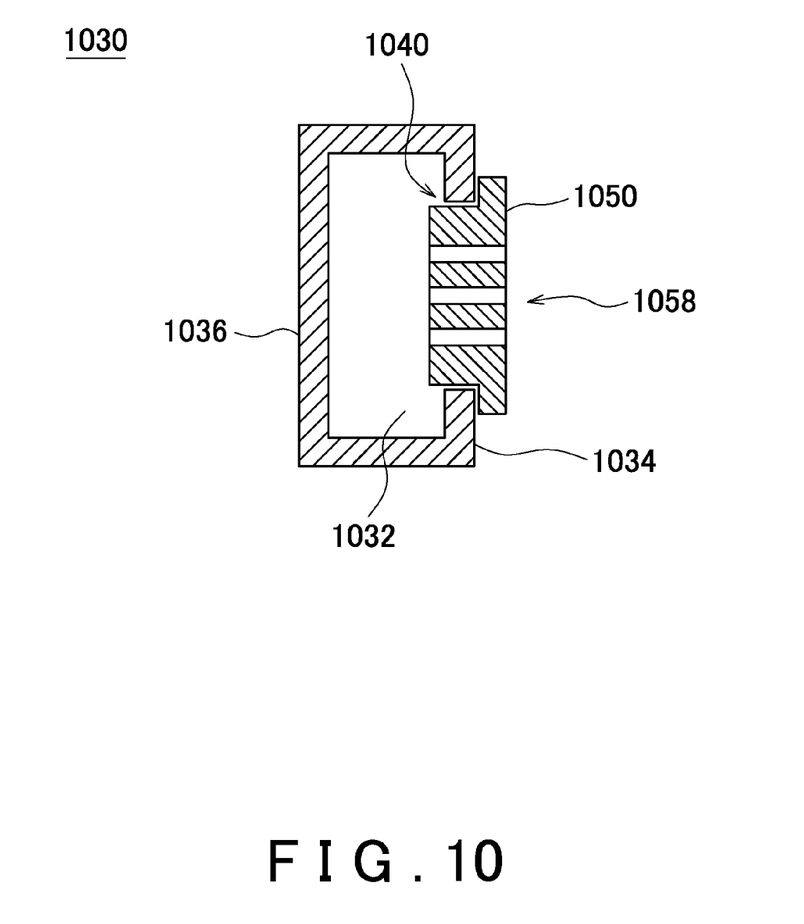
FIG. 10 schematically shows an exemplary cross section of a liquid container 1030.

FIG. 10 schematically shows an exemplary cross section of a liquid container 1030. The top of the frame 120 in which the liquid container 1030 is disposed when worn on the head is shown at the top in FIG. 10. The liquid container 1030 can be inserted to and removed from the frame 120. The liquid container 1030 may have the same configuration as the liquid container 130, and a redundant description of this configuration is omitted. The liquid container 1030 may be an example of a liquid storage portion.

A cavity 1032 that can store liquid is formed within the liquid container 1030. The liquid container 1030 includes a side surface 1034 that is disposed on the inside surface of the frame 120 when the frame 120 in which the liquid container 1030 is disposed is worn on the head, and a side surface 1036 opposite the side surface 1034.

The liquid container 1030 differs from the liquid container 130 in that the side surface 1034 includes an opening 1040. The liquid container 1030 also differs from the liquid container 130 in that the liquid container 1030 includes a lid 1050 that blocks the opening 1040. The lid 1050 includes a gas permeable hole 1058 that penetrates through the lid 1050 and allows gas to pass therethrough while not allowing liquid to pass therethrough. The lid 1050 and the gas permeable hole 1058 may be an example of a gas passing section. Concerning the remaining configuration, the cavity 1032, the side surface 1034, the side surface 1036, and the gas permeable hole 1058 may be have the same configuration as the cavity 132, the side surface 134, the side surface 136, and the gas permeable hole 138 of the liquid container 130. Descriptions of other components that are the same as those in the liquid container 130 are omitted.

The opening 1040 penetrates through the side surface 1034 to connect the cavity 1032 to the outside of the liquid container 1030. As a result, liquid is restricted from flowing into the cavity 1032 from the opening 1040. The lid 1050 blocks the opening 1040, thereby restricting leakage of the liquid from the opening 1040. The material used for the lid 1050 may be an elastomer such as natural rubber, synthesized rubber, or silicone rubber.

In FIG. 10, for ease of explanation, a gap is shown between the lid 1050 and the walls of the opening 1040. However, the lid 1050 and the opening 1040 may be designed to have any desired shape.

In the present embodiment, the gas permeable hole 1058 is formed in the lid 1050, but the lid 1050 is not limited to this configuration. The lid 1050 may include an organic polymer film or an inorganic porous film that allows gas to pass therethrough but does not allow liquid to pass therethrough. In the present embodiment, the lid 1050 is made of an elastomer, but the lid 1050 is not limited to this. If the lid 1050 is arranged at a position that is above the position of the liquid surface when the frame 120 in which the liquid container 1030 is disposed is worn on the head, the lid 1050 may be made of a water retentive or water absorbent material such as felt, paper, a sea sponge, a sponge, a hydrophilic polymer, or a hydrogel.

Figure 11:
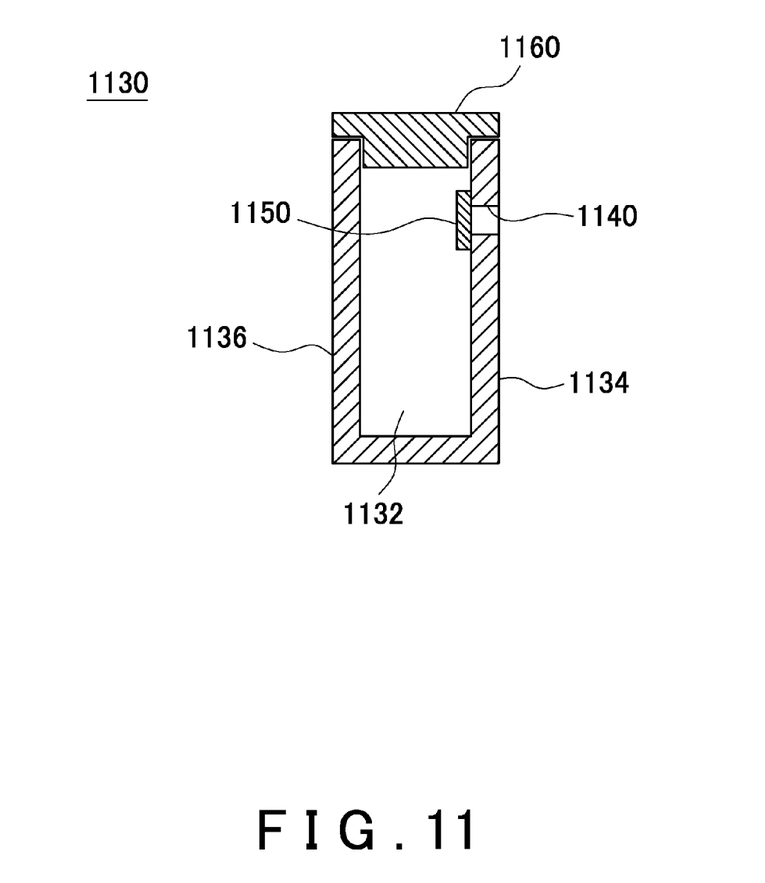
FIG. 11 schematically shows an exemplary cross section of a liquid container 1130.

FIG. 11 schematically shows an exemplary cross section of a liquid container 1130. The top of the frame 120 in which the liquid container 1130 is disposed when worn on the head is shown at the top in FIG. 11. The liquid container 1130 can be inserted to and removed from the frame 120. The liquid container 1130 may have the same configuration as the liquid container 130, and a redundant description of this configuration is omitted. The liquid container 1130 may be an example of a liquid storage portion.

A cavity 1132 that can store liquid is formed within the liquid container 1130. The liquid container 1130 includes a side surface 1134 that is disposed on the inside surface of the frame 120 when the frame 120 in which the liquid container 1130 is disposed is worn on the head, and a side surface 1136 opposite the side surface 1134.

The liquid container 1130 includes an opening 1140 in the side surface 1134. The opening 1140 penetrates through the side surface 1134 to connect the cavity 1132 to the outside of the liquid container 1130. The liquid container 1130 differs from the liquid container 1030 and the liquid container 130 in that the liquid container 1130 includes a water holding portion 1150 that blocks the opening 1140. The liquid container 1130 further differs from the liquid container 1030 and the liquid container 130 in that an opening is formed in the top portion of the liquid container 1130 and this opening is blocked by a lid 1160. Aside from these differences, the cavity 1132, the side surface 1134, and the side surface 1136 may have the same configuration as the cavity 132, the side surface 134, and the side surface 136 of the liquid container 130.

The water holding portion 1150 blocks the opening 1140. The water holding portion 1150 may include a water retentive or water absorbent material such as felt, paper, a sea sponge, a sponge, a hydrophilic polymer, or a hydrogel. Even when the opening 1140 is large and cannot prevent leakage of liquid from the cavity 1132 by itself, providing the water holding portion 1150 can restrict the leakage of the liquid from the cavity 1132 to some degree.

The water holding portion 1150 is disposed on the surface of the side surface 1134 that faces away from the inside surface of the frame 120. As a result, the water holding portion 1150 can be restricted from touching the face of the wearer. The top end of the water holding portion 1150 may be arranged to be above the liquid surface of the liquid stored in the cavity 1132. As a result, a region is formed through which gas can pass in a portion of the water holding portion 1150. Furthermore, the leakage of the liquid from the opening 1140 can be restricted.

The volume occupied by the water holding portion 1150 within the cavity 1132 may be less than half the volume of the cavity 1132. As a result, a greater amount of liquid can be stored within the cavity 1132. Furthermore, with this configuration, it is easier for the water holding portion 1150 to remain dry than when the water holding portion 1150 is disposed in the entire cavity 1132. As a result, the eyewear can be used hygienically. The opening 1140 and the water holding portion 1150 may be an example of a gas passing section.

In FIG. 11, for ease of explanation, a gap is shown between the lid 1160 and the side surface 1134 and between the lid 1160 and the side surface 1136. However, the lid 1160, the side surface 1134, and the side surface 1136 may be designed to have any desired shape.

Figure 12:
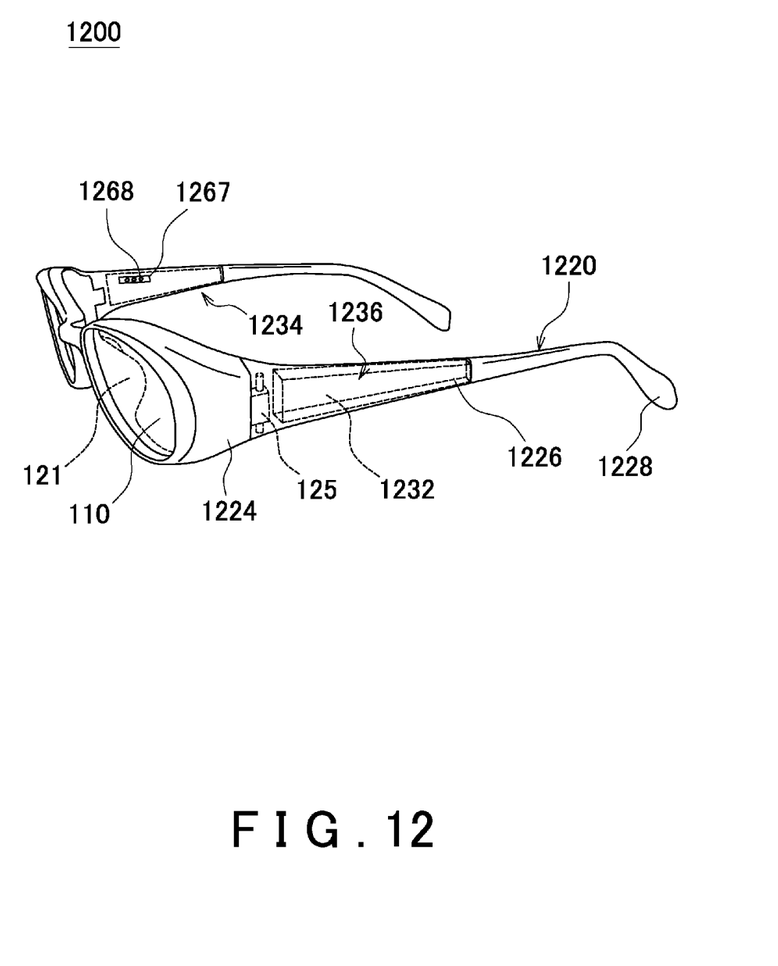
FIG. 12 is a schematic view of glasses 1200.
Figure 13:
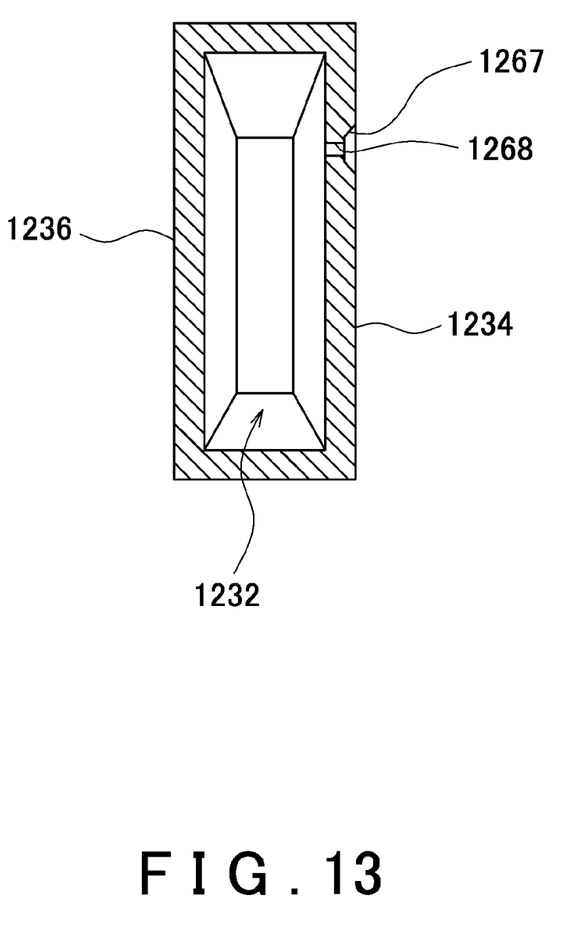
FIG. 13 schematically shows an exemplary cross section of the glasses 1200.

FIG. 12 is a schematic view of glasses 1200. FIG. 13 schematically shows an exemplary cross section of the glasses 1200. FIG. 13 shows the cross section of the glasses 1200 as seen from the left side when the frame 1220 is cut by a plane that is parallel to the vertical direction of FIG. 12 and perpendicular to the side surface 1234. The following describes the glasses 1200 using FIGS. 12 and 13.

The glasses 1200 includes the pair of lenses 110 and the frame 1220. The glasses 1200 and the frame 1220 may be an example of eyewear. The frame 1220 may include the nose pad 121, the rim 122, an end piece 1224, the hinge 125, a temple 1226, and an ear band 1228.

The glasses 1200 differ from the glasses 100 in that an opening is not formed in the end piece 1224. The glasses 1200 further differ from the glasses 100 in that a cavity 1232 is formed within the temple 1226. Components that are the same as those of the glasses 100 are given the same reference numerals, and further description is omitted.

A pair of temples 1226 sandwich the head of the wearer. Each temple 1226 may be an example of a liquid storage portion. A cavity 1232 that can store liquid is formed in at least one of the temples 1226. The inner surface of the cavity 1232 may be processed to be water repellent. The inner surface of the cavity 1232 may also undergo antibacterial processing.

Each temple 1226 includes a side surface 1234 that is arranged on the side facing the head of the wearer, when the frame 1220 is worn (referred to hereinafter as the "inside" of the frame 1220), and a side surface 1236 that is arranged opposite the side surface 1234. A recessed portion 1267 is formed in the side surface 1234. The recessed portion 1267 includes a gas permeable hole 1268 that penetrates from the cavity 1232 to the side surface 1234 and that allows gas to pass therethrough but does not allow liquid to pass therethrough. The gas permeable hole 1268 may be an example of a gas passing section. The gas permeable hole 1268 may have the same configuration as the gas permeable hole 138.

The ear band 1228 covers at least a portion of the temple 1226. In the present embodiment, the ear band 1228 may cover the opening that connects the cavity 1232 inside the temple 1226 to the outside of the temple 1226. The ear band 1228 may be inserted into the opening. The ear band 1228 may be attached to and unattached from the temple 1226. As a result, the liquid can be supplied to the cavity 1232 within the temple 1226 by removing the ear band 1228.

With the above configuration, the gas generated by the evaporation of the liquid stored in the cavity 1232 can pass through the gas permeable hole 1268 to be supplied to the inside of the frame 1220. Furthermore, since the gas permeable hole 1268 does not allow the liquid stored in the cavity 1232 to pass therethrough, the liquid is restricted from splashing on the face of the wearer.

In the present embodiment, the cavity 1232 is formed within the temple 1226, but the liquid storage portion is not limited to this configuration. The cavity may be formed within the nose pad, the rim, the end piece, or the ear band.

In the present embodiment, the gas permeable hole 1268 is used as an example of the gas passing section, but the gas passing section is not limited to this example. The gas passing section may include an organic polymer film or an inorganic porous film that allows gas to pass therethrough but does not allow liquid to pass therethrough. The gas passing section may include an organic polymer film or an inorganic porous film that allows water vapor to pass therethrough but does not allow pure water or tap water to pass therethrough. The gas passing section may be silicone rubber.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. Eyewear comprising:
    a frame; and
    a liquid storage portion that is disposed within the frame and that includes a cavity for storing liquid in a non-absorbed state, wherein
    the liquid storage portion includes a gas permeable hole that is formed in an inside surface thereof, which is a surface facing a head of a wearer when the frame is worn on the head, that penetrates from the cavity to the inside surface of the liquid storage portion, and that allows gas to pass therethrough but does not allow liquid to pass therethrough.

2. The eyewear according to claim 1, wherein
    the liquid storage portion is disposed such that an outer surface of the liquid storage portion is further inside the frame than an outer surface of the frame.

3. The eyewear according to claim 1, wherein
    the liquid storage portion is detachable from the frame.

4. The eyewear according to claim 1, wherein
    the frame includes a rim that supports a lens, the rim including a hood portion that extends from a periphery of the lens toward the wearer.

5. The eyewear according to claim 1, wherein
the liquid storage portion further includes an opening in the inside surface thereof and a lid that blocks the opening, the gas permeable hole being formed in the lid.

6. The eyewear according to claim 5, wherein
the lid is made of an elastomer.

7. The eyewear according to claim 1, wherein
the frame includes a temple and an ear band that covers a portion of the temple,
the liquid storage portion is disposed in the temple, and
the portion of the temple covered by the ear band includes an opening that connects the cavity of the liquid storage portion to outside of the temple, such that liquid can be supplied to the cavity by removing the ear band.

8. The eyewear according to claim 1, wherein
the liquid storage portion further includes a water retentive or water absorbent material.

9. The eyewear according to claim 8, wherein
the water retentive or water absorbent material occupies less than half the volume of the cavity.

10. The eyewear according to claim 1, wherein
a plurality of the gas permeable holes are formed in the inside surface of the liquid storage portion, and
when the frame is worn on the head, distance from a bottommost portion of the gas permeable holes to a bottommost portion of a component of the frame that the liquid storage portion is disposed in is greater than distance from a topmost portion of the gas permeable holes to a topmost portion of the component of the frame that the liquid storage portion is disposed in.

11. The eyewear according to claim 10, wherein
the liquid storage portion is disposed such that an outer surface of the liquid storage portion is further inside the frame than an outer surface of the frame.

12. The eyewear according to claim 10, wherein
the liquid storage portion is detachable from the frame.

13. The eyewear according to claim 10, wherein
the frame includes a rim that supports a lens, the rim including a hood portion that extends from a periphery of the lens toward the wearer.

14. The eyewear according to claim 10, wherein
the liquid storage portion includes an opening in the inside surface thereof and a lid that blocks the opening, the gas permeable hole being formed in the lid.

15. The eyewear according to claim 14, wherein
the lid is made of an elastomer.

16. The eyewear according to claim 10, wherein
the component of the frame that the liquid storage portion is disposed in is a temple, an ear band, or an end piece of the frame.

17. The eyewear according to claim 16, wherein
the shape of the inside surface of the liquid storage portion conforms to the shape of the component of the frame that the liquid storage portion is disposed in.

18. Eyewear comprising:
a frame; and
a liquid storage portion that is disposed within the frame and that includes a cavity for storing liquid, wherein
the liquid storage portion includes a gas permeable hole that is formed in an inside surface thereof, which is a surface facing a head of a wearer when the frame is worn on the head, that penetrates from the cavity to the inside surface of the liquid storage portion, and that allows gas to pass therethrough but does not allow liquid to pass therethrough, and
the liquid storage portion further includes an opening in the inside surface thereof and a lid that blocks the opening, the gas permeable hole being formed in the lid.

19. The eyewear according to claim 18, wherein
the lid is made of an elastomer.

20. The eyewear according to claim 18, wherein
the shape of the inside surface of the liquid storage portion conforms to the shape of a component of the frame that the liquid storage portion is disposed in.

21. Eyewear comprising:
a frame; and
a liquid storage portion that is disposed within the frame and that includes a cavity for storing liquid, wherein
the liquid storage portion includes a gas permeable hole that is formed in an inside surface thereof, which is a surface facing a head of a wearer when the frame is worn on the head, that penetrates from the cavity to the inside surface of the liquid storage portion, and that allows gas to pass therethrough but does not allow liquid to pass therethrough,
the frame includes a temple and an ear band that covers a portion of the temple,
the liquid storage portion is disposed in the temple, and
the portion of the temple covered by the ear band includes an opening that connects the cavity of the liquid storage portion to outside of the temple, such that liquid can be supplied to the cavity by removing the ear band.

22. The eyewear according to claim 21, wherein
the liquid storage portion is disposed such that an outer surface of the liquid storage portion is further inside the frame than an outer surface of the frame.

23. The eyewear according to claim 21, wherein
the shape of the inside surface of the liquid storage portion conforms to the shape of the temple.

* * * * *